US008012113B2

(12) United States Patent
Lee et al.

(10) Patent No.: US 8,012,113 B2
(45) Date of Patent: Sep. 6, 2011

(54) SPINAL BRACE

(75) Inventors: Bert T. Lee, Paramus, NJ (US); John J. Lee, Fort Lee, NJ (US)

(73) Assignee: Disc Disease Solutions, Inc., Ridgefield, NJ (US)

( * ) Notice: Subject to any disclaimer, the term of this patent is extended or adjusted under 35 U.S.C. 154(b) by 102 days.

(21) Appl. No.: 11/737,910

(22) Filed: Apr. 20, 2007

(65) Prior Publication Data

US 2008/0234617 A1    Sep. 25, 2008

Related U.S. Application Data

(60) Provisional application No. 60/894,283, filed on Mar. 12, 2007.

(51) Int. Cl.
*A61F 5/00* (2006.01)
*A61F 5/24* (2006.01)
*A61B 17/00* (2006.01)

(52) U.S. Cl. ............. 602/19; 128/96.1; 602/32; 602/12; 602/13; 606/201; 606/237; 606/240; 606/241

(58) Field of Classification Search ............... 602/19, 602/6, 5, 1, 13, 12; 128/96.1, 99.1, 100.1, 128/102.1, 869, 876; 606/241, 201, 237, 240; 2/244

See application file for complete search history.

(56) References Cited

U.S. PATENT DOCUMENTS

| 5,728,055 | A | * | 3/1998 | Sebastian | 602/19 |
| 5,950,628 | A | * | 9/1999 | Dunfee | 602/19 |
| 5,980,560 | A | | 11/1999 | Chang | |
| 7,618,509 | B2 | | 11/2009 | Chang | |
| 2004/0097857 | A1 | * | 5/2004 | Reinecke et al. | 602/19 |
| 2007/0197943 | A1 | * | 8/2007 | Hakonson et al. | 602/13 |

* cited by examiner

*Primary Examiner* — Patricia M Bianco
*Assistant Examiner* — Tarla R Patel
(74) *Attorney, Agent, or Firm* — Cantor Colburn LLP (57) ABSTRACT

A spinal brace includes a flexible air injectable band configured to be disposed about a torso of a user and to provide traction to a spine of the user, at least one support panel configured to provide support by compression to at least a region of the torso, the at least one support panel being less flexible than the air injectable band, and at least one means of associating the at least one support panel with the flexible air injectable band.

19 Claims, 15 Drawing Sheets

SPINAL BRACE

CROSS REFERENCE TO RELATED APPLICATION

This application is related to and claims the benefit of U.S. Provisional Patent Application Ser. No. 60/894,283 filed on 12 Mar. 2007, the entire contents of which are herein incorporated by reference.

TECHNICAL FIELD OF INVENTION

The disclosure relates generally to a spinal brace, and more particularly to a spinal brace that provides support and decompression.

BACKGROUND OF THE INVENTION

Traditional spinal braces are used as a method of minimizing pain and inducing healing after an injury or spinal surgery. Braces are used to provide stabilization of the patients lumbar region and provide support to the involved spinal structural tissues.

There are a variety of spinal braces available. Each has features that achieve that are beneficial to the wearer of the brace. These features can be related to comfort to the wearer, ease of use to the wearer, and cost, which also varies in degree. In most instances, one or more of these features are compromised to enhance the other features.

For example, it is generally is accepted that a custom-made spinal brace is believed to provide the highest degree of stabilization and support. However, custom made braces have disadvantages in comfort and lack of adjustability. Adjustable devices, on the other hand, comprise elastic features for support, and thus, are more comfortable and usable by patients of different sizes. However, many of these braces offer a lesser degree of support and stabilization.

There are also spinal braces that are referred to as custom-fit braces. These braces include pre-manufactured parts that allow some room for movement for fitting patient's of different sizes. These braces may fit better for the individual but many of custom-fit braces rely on flexible non-rigid parts to achieve a degree of adjustability. Fitting for comfort may compromise immobilization and support for the lumbar spine.

As such, a brace that provides immobilization, support, vertebral decompression, comfort, and ease of use is desirable.

SUMMARY OF THE INVENTION

A spinal brace includes a flexible air injectable band configured to be disposed about a torso of a user and to provide traction to a spine of the user, at least one support panel configured to provide support by compression to at least a region of the torso, the at least one support panel being less flexible than the air injectable band, and at least one means of associating the at least one support panel with the flexible air injectable band.

BRIEF DESCRIPTION OF THE FIGURES

The following descriptions should not be considered limiting in any way. With reference to the accompanying drawings, like elements are numbered alike.

DETAILED DESCRIPTION OF THE INVENTION

Figure 5:
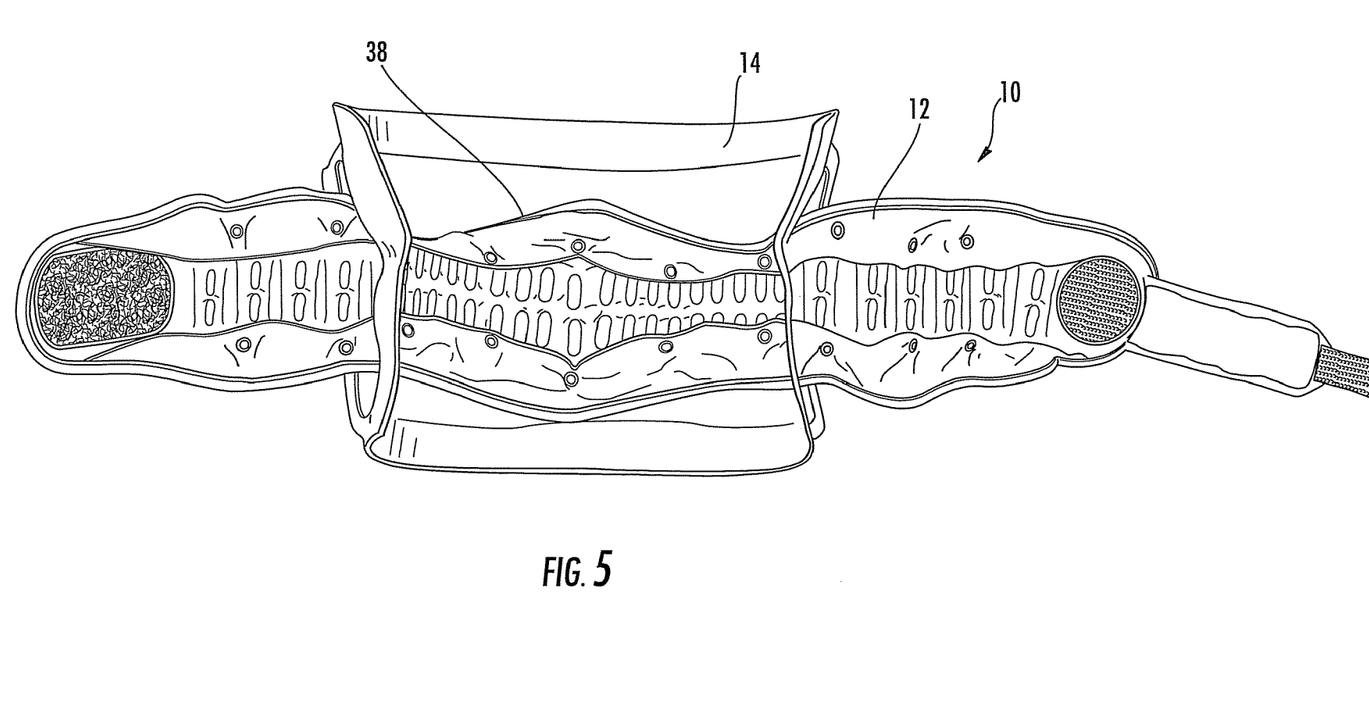
FIG. 5 is the view of the spinal brace of FIG. 3, including a band in a compressed state.
Figure 6:
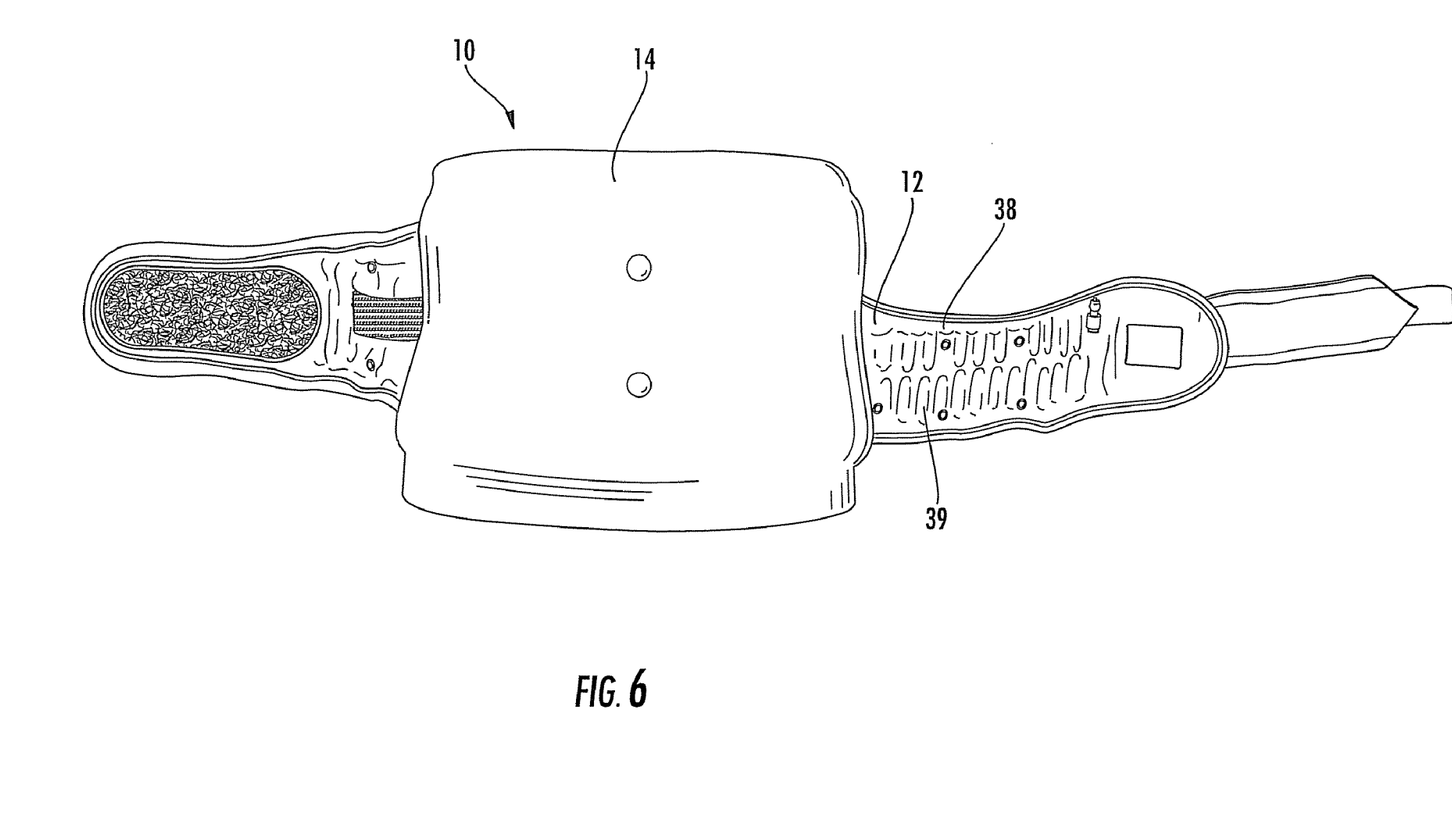
FIG. 6 is the view of the spinal brace of FIG. 4, including a band in a compressed state.
Figure 7:
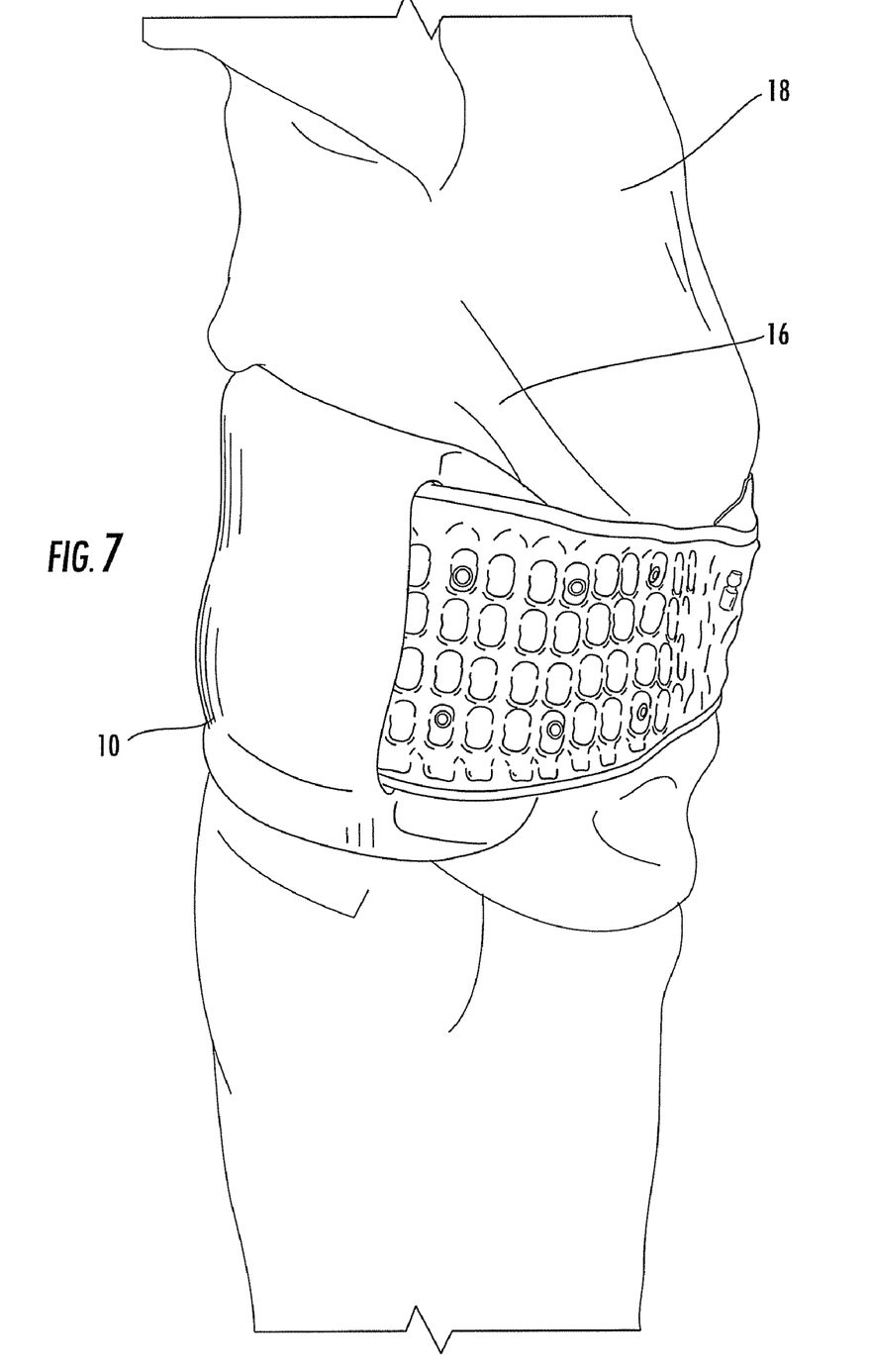
FIG. 7 is a side view of the spinal brace disposed about a user.
Figure 8:
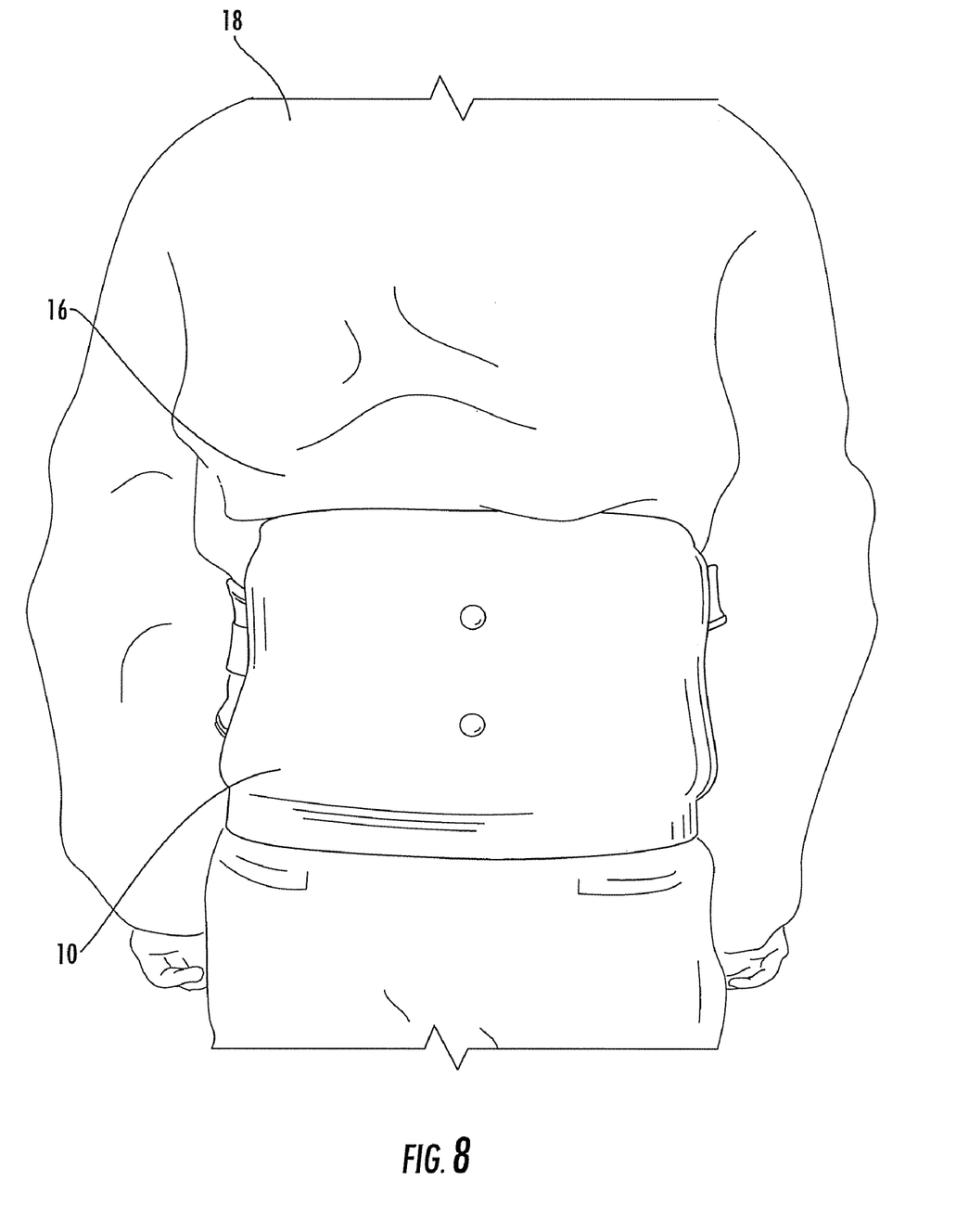
FIG. 8 is a rear view of the spinal brace disposed about the user of FIG. 7.
Figure 9:
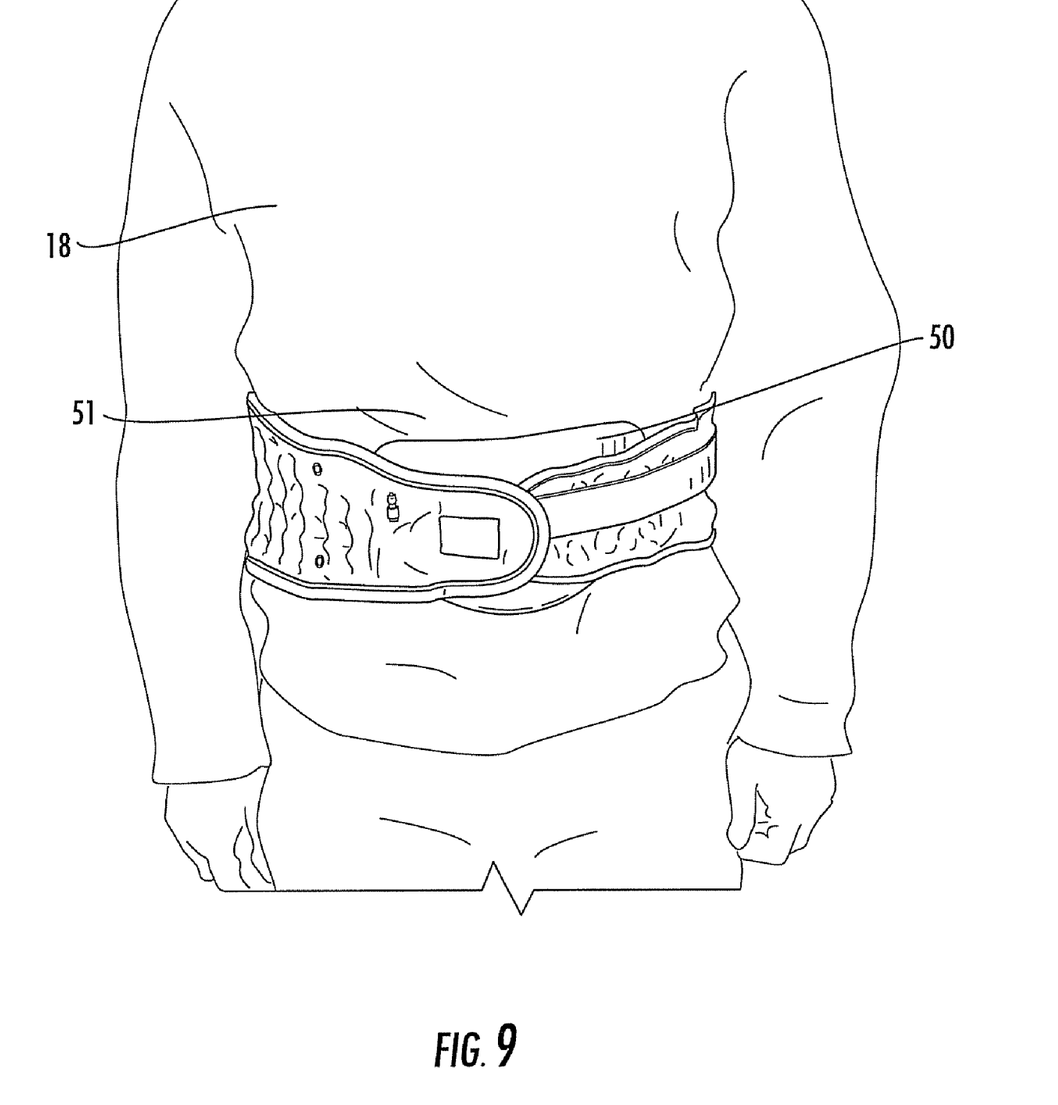
FIG. 9 is a frontal view of the spinal brace disposed about the user of FIG. 7.

Referring to FIGS. 1-12, a spinal brace 10 is illustrated. The spinal brace 10 includes a flexible air injectable band 12 and at least one support panel 14. The air injectable band 12 is configured to be disposed about a torso 16 of a user 18, as shown in FIGS. 7-9. The at least one support panel 14 is configured to provide support to at least a region 20 of the torso 16 (such as a lower back/lumbar region) of the user 18, as shown best in FIGS. 7 and 8), and comprises a material that is less flexible than the material comprising the air injectable band 12. The at least one support panel 14 also includes at least one means 23a-b and 24 of associating the at least one support panel 14 with the air injectable band 12.

Figure 1:
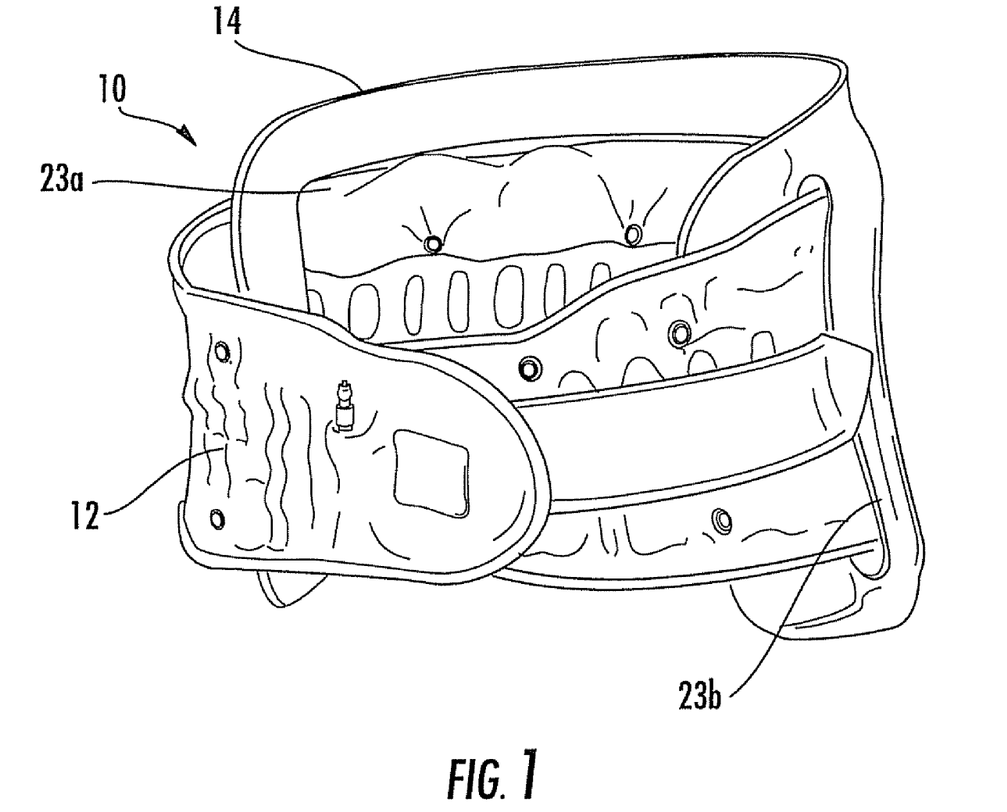
FIG. 1 is a top perspective view of a spinal brace.
Figure 2:
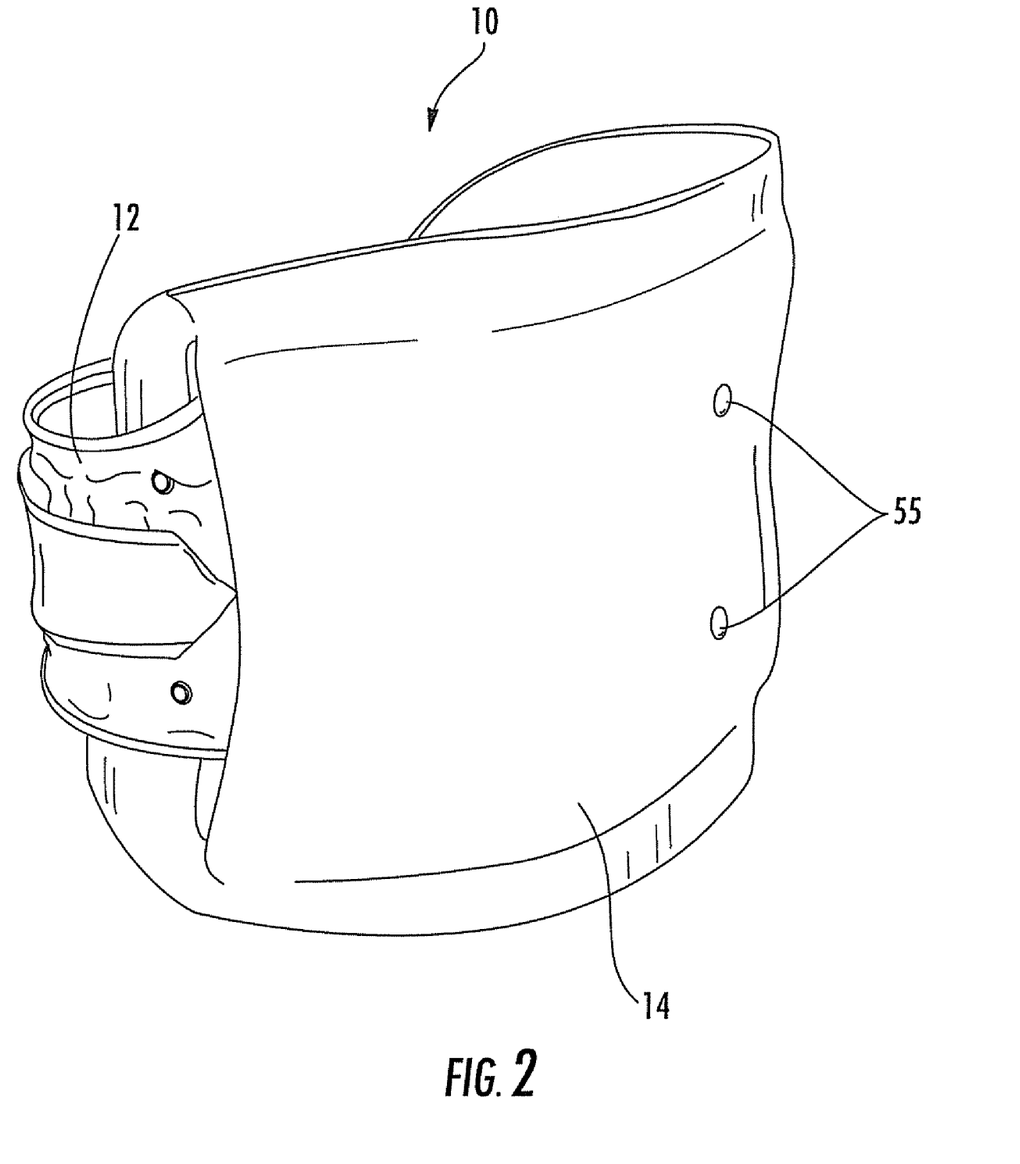
FIG. 2 is a another top perspective view of the spinal brace.
Figure 3:
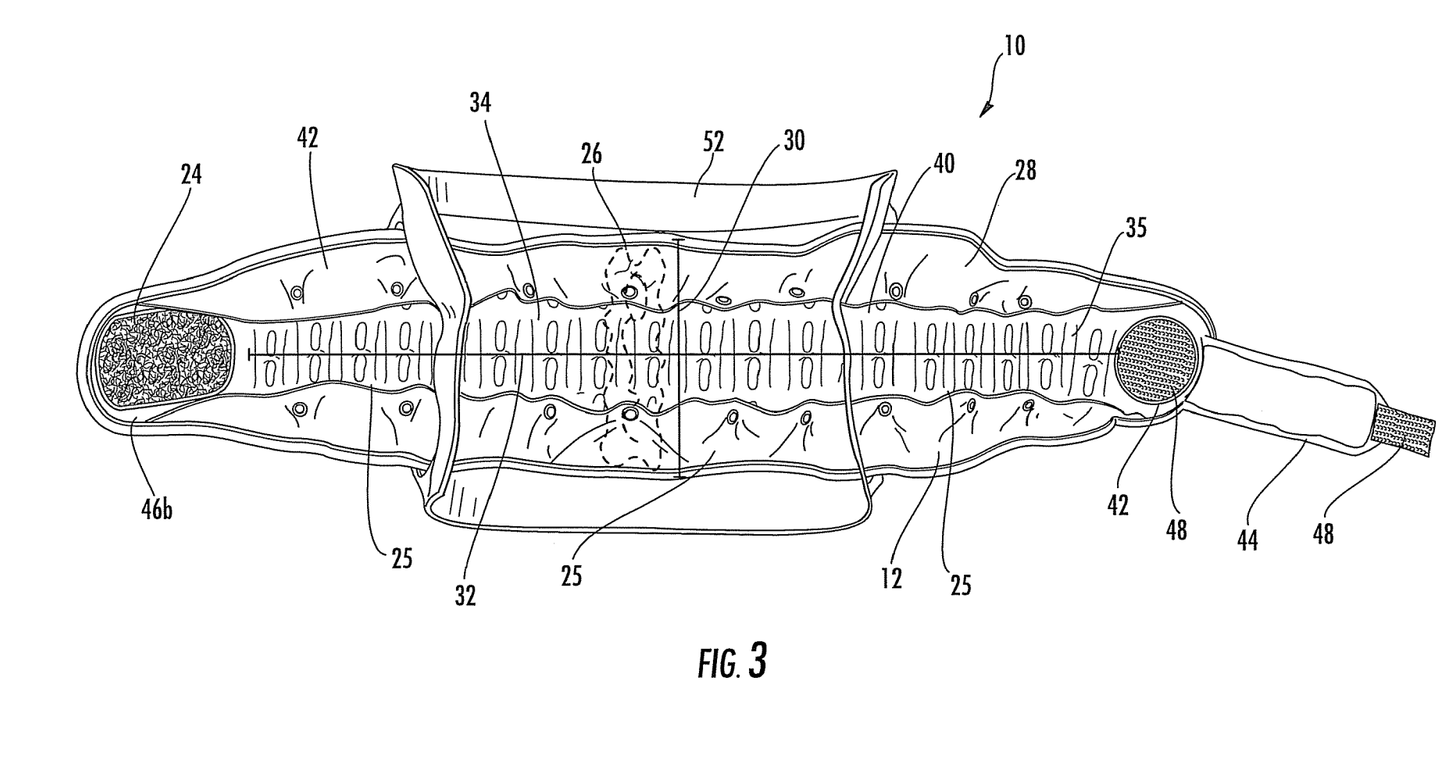
FIG. 3 is a planar view of the spinal brace of FIGS. 1 and 2.
Figure 4:
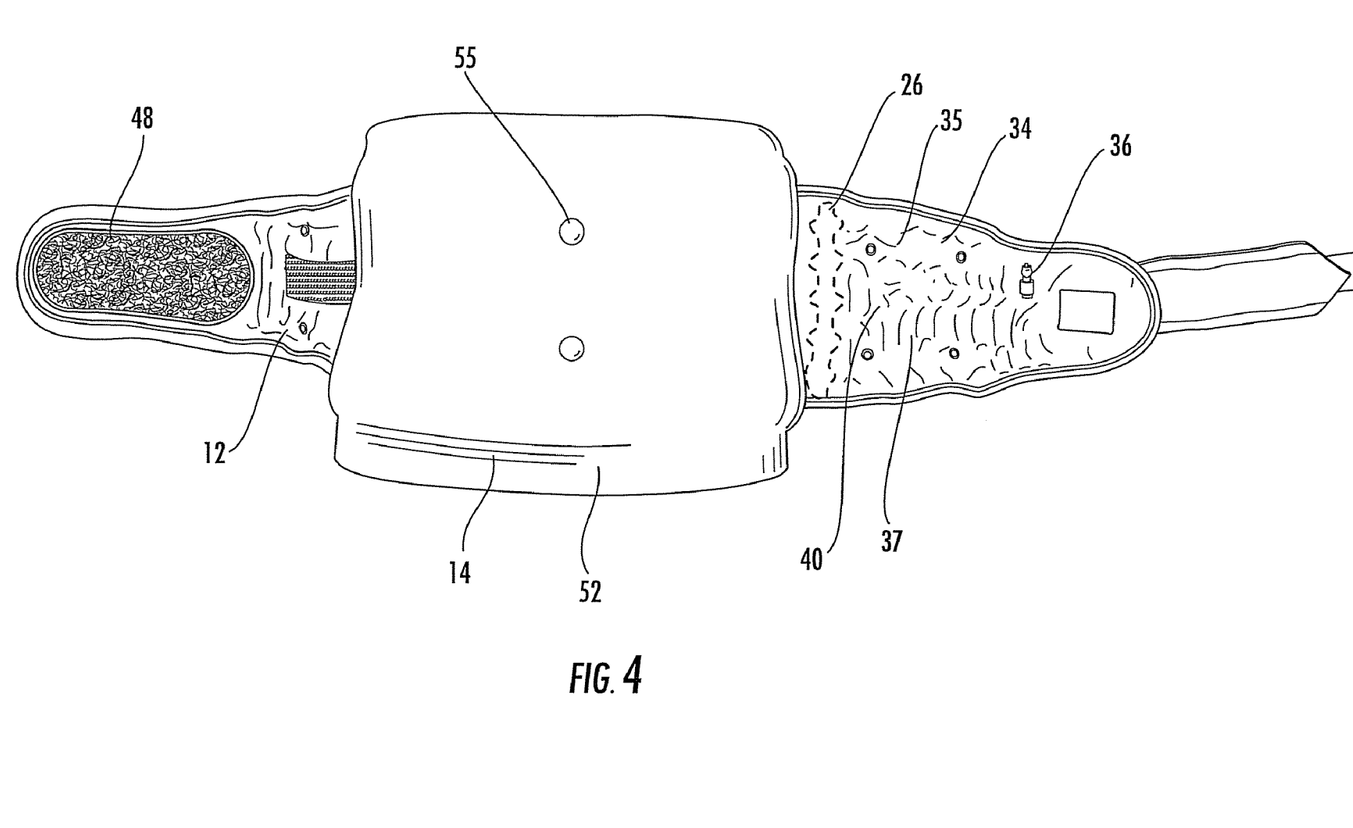
FIG. 4 is another planar view of the spinal brace of FIGS. 1 and 2.

Referring to FIGS. 3 and 4 in particularly, an exemplary embodiment of the air injectable band 12 will now be discussed in detail. In this exemplary embodiment, the air injectable band 12 includes an expandable portion 25, an air injectable tube 26, and a securing cover 28. The air injectable tube 26 is disposed within and attached to the securing cover 28. The attachment of the tube 26 to the cover 28 is achieved via any means desirable, such as stitching, adhesive, or any type of fastener. As shown best in FIG. 3, the tube 26 extends substantially across a vertical and horizontal extent 30 and 32 of the expandable portion 25, with the vertical extent 30 being greatest at a relative middle 20 of the expandable portion 25.

As shown in FIGS. 3 and 4, the tube 26 is disposed within the cover 28 in a grid pattern 34 across the horizontal extent 32 of the expandable portion 25. The grid pattern 34 allows the tube 26 to include substantially vertically disposed ribs 35 and substantially horizontally disposed connectors 37 that fluidly connect the ribs 15. The tube 26 comprises an elastic material, and includes an air inlet and exit valve 36 (such as a pressure valve) installed at one end. The valve 36 extends from the cover 28 and is configured to associate with an air injection device, such as a pump (not illustrated). Air is injected into and released from the tube 26, and band 12 in general, via this valve 36. Prior to air injection into the tube 26 via the valve 36, the tube 26 and band 14 are in a relaxed state 38. As shown in FIGS. 5 and 6, when there is no air in the tube 26, the elasticity of the tube 26 contracts the expandable portion 25 of the band 12 into the relaxed state 38. This is accomplished via the attachment of the elastic tube 26 to the cover 28. This contracting of the expandable portion 25 creates wrinkles 39 in the cover 28, as is shown in the Figure.

When air is inlet into the tube 26, the grid pattern 34 of the tube 26 (particularly the ribs 35 of the tube 26) expands vertically. As more air is injected into the tube 26, the vertical expansion becomes greater, and can continue until the tube 12 reaches an expanded/elastic limit. Again, due to the attachment of the tube 26 to the cover 28, expansion of the tube 26 causes expansion of the expandable portion 25. This vertical expansion of both the tube 26 and expandable portion 25 aids in increasing intervals between intervertebral discs of the user 18, providing a decompression of vertebrae within the user's vertebral column. As shown in FIGS. 3 and 4, the ribs 35 of the tube 26 (when expanded) are also configured to include intervalled ridges 40 that further aid in increasing intervals between intervertebral discs of the user 18. When the valve 36 is release to allow air to exit the tube 26, the elasticity of the tube 26 will cause the tube 26 and expandable portion 25 to return to the relaxed state 38.

It should be appreciated that at least an inner surface 42 (i.e., surface that contacts the user 18) of the cover 28 comprises a non-abrasive material, such as cotton, while the outer surface comprises polyurethane. It should also be appreciated that an elastic securing strap 44 extends from at least one end of the band 12, wherein the inner surface 42 of the end, outer surface of the opposite end 46b, and securing strap 44 include a means 48 for securing the band 12 (and brace 10 in general) around the torso 16 of the user 18. The means 48 for securing is at least one of a hook and loop attachment/detachment arrangement, such as that commonly known as VELCRO®, at least one snap, at least one belt, and/or at least one button.

It should be further appreciated that the tube 26 may comprise any pattern desirable to vertical expansion of the expandable portion 25 (and decompression of the vertebrae). The tube 26 may also comprise multiple tubes or tube portions fluidly connected with each other (such as via one connecting tube) to form the grid pattern 34, or any other pattern desirable to vertical expansion (and decompression of the vertebrae) of the expandable portion 25, such as a serpentine pattern. It should be still further appreciated that at least part of the cover 28 may comprise an elastic material, with the tube 26 being created in the elastic cover 28 via a patterned stitching (or applied adhesive) of the cover 28. Stitching or adhesive application of this kind may be used to create the grid pattern 34 (or any other pattern desirable to vertical expansion of the expandable portion 25 and decompression of the vertebrae) within the cover 28. The at least part of the cover that comprises the elastic material may then be covered at its inner surface with a non-abrasive material such as cotton.

It should be additionally appreciated that elastic material may be added within or about the cover 28 to aid in overall elasticity of the expandable portion 25. Addition of this elastic material (such as elastic bands or strips) may be included with an elastic or non-elastic cover 28, as well as an elastic or non-elastic tube 26.

Referring to FIGS. 3-12, the at least one support panel 14 will now be discussed. In an exemplary embodiment, the at least one support panel 14 comprises an anterior panel 50 and a posterior panel 52. The anterior panel 50 includes a geometry 54 configured to conform to a stomach 51 of the user 18. The posterior panel 52 includes a geometry 56 configured to conform to at least a portion of a back 58 of the user 18. These geometries 54 and 56 are configured to provide support to the user's back (particularly lumbar) region and may assume any shape and thickness and may be composed of any material sufficient to provide such support. The shape of the geometries 54 and 56 shown in the various Figures is provided by way of non-limiting example. Furthermore, both panels 50 and 52 may generally be composed of a rigid or semi-rigid material, such as plastic or fiberglass. Both panels 50 and 52 also may include inner surfaces 68a and 68b that are lined with a soft material 70, such as a foam.

Figure 10:
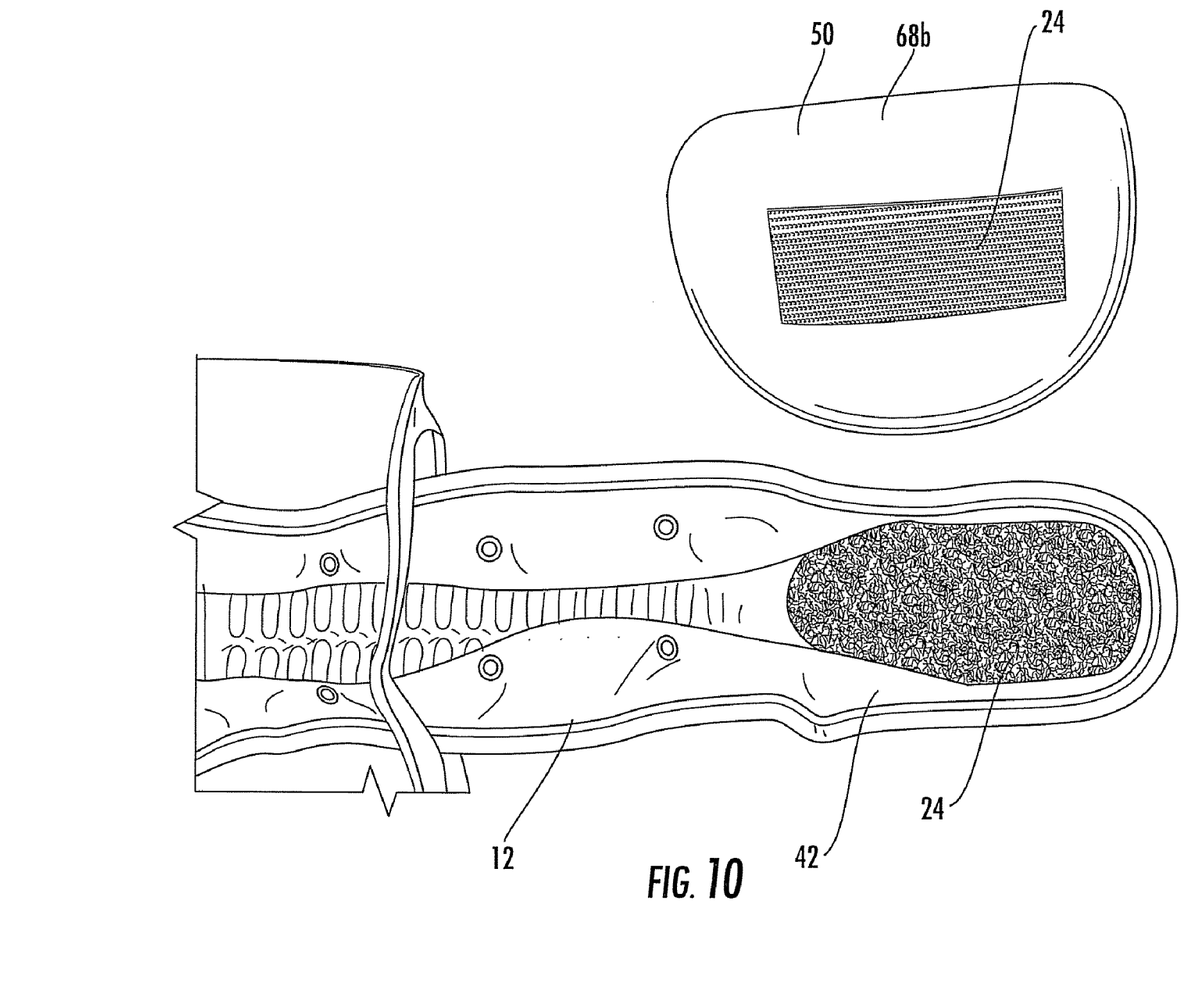
FIG. 10 is a planar view of one means of associating at least one support panel of the spinal brace with a band of the spinal brace.
Figure 11:
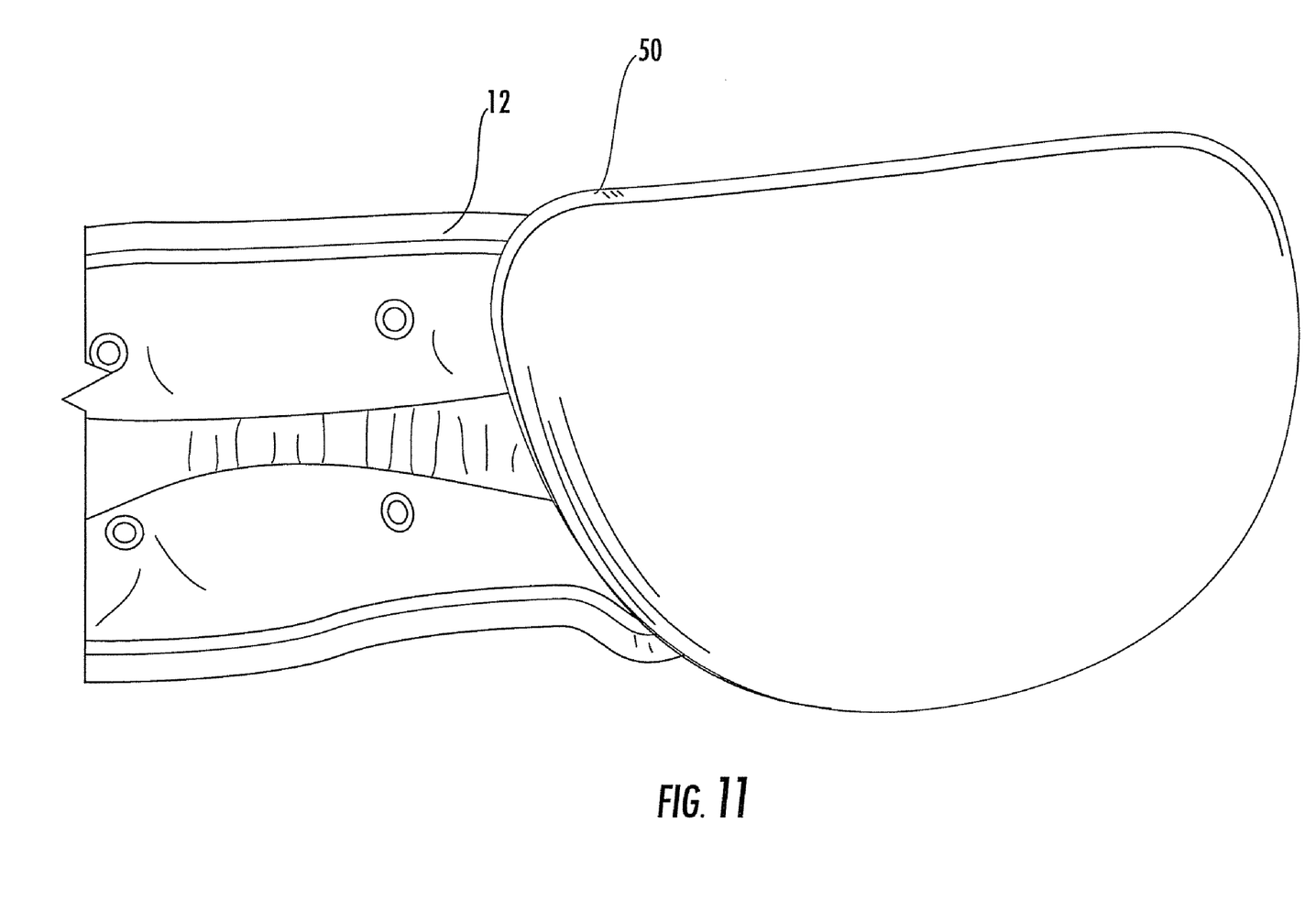
FIG. 11 is a planar view the at least one support panel of the spinal brace associated with the band of the spinal brace.
Figure 12:
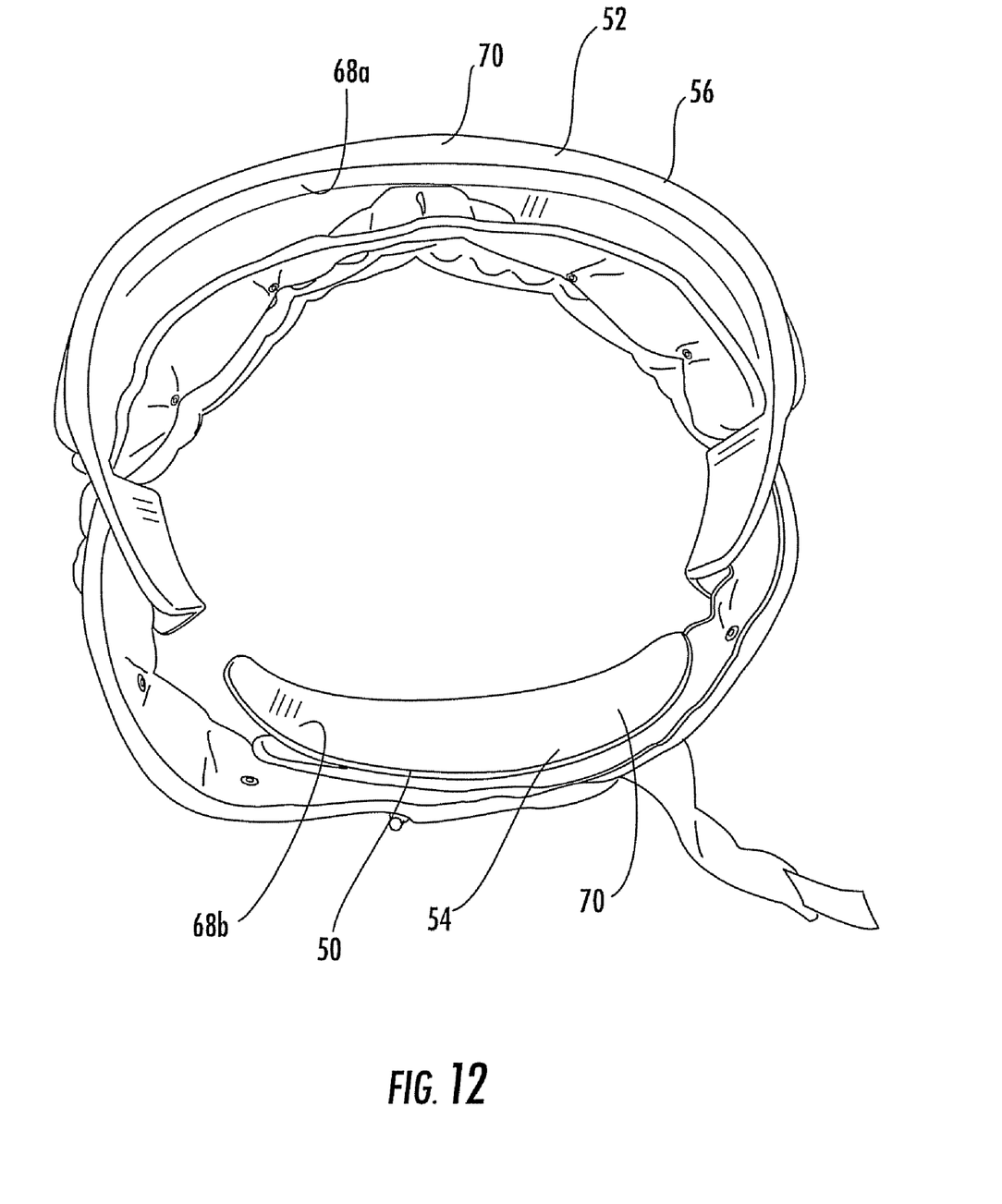
FIG. 12 is a top view of the spinal brace of FIGS. 1 and 2.

As is shown best in FIGS. 1-3 and 12, the means 24 of associating the anterior panel 52 with the air injectable band 12 (in an exemplary embodiment) are two associating openings 23a-b disposed at substantially opposite ends of the posterior panel 52. As shown in these Figures, the securing strap 44 and ends of the band 12 are inserted from the inner surface 68a of the panel 52 through the openings 23a-b of the panel 52, so as to associate the panel 52 with the band 12. One exemplary end of the band 12 is shown at item 46b in FIG. 3. The band 12 is further attached to the panel 52 via fasteners 55. Referring particularly to FIGS. 10 and 11, the means 24 of associating the anterior panel 50 with a relative front portion of the band 12 is illustrated, and may be accomplished via any desirable means, such as VELCRO® or snaps. In an embodiment using VELCRO® (such as the embodiment illustrated), the associable VELCRO® strips are respectively disposed on the inner surface 68b of the anterior panel 50 and on the inner surface of the band 12.

Figure 13:
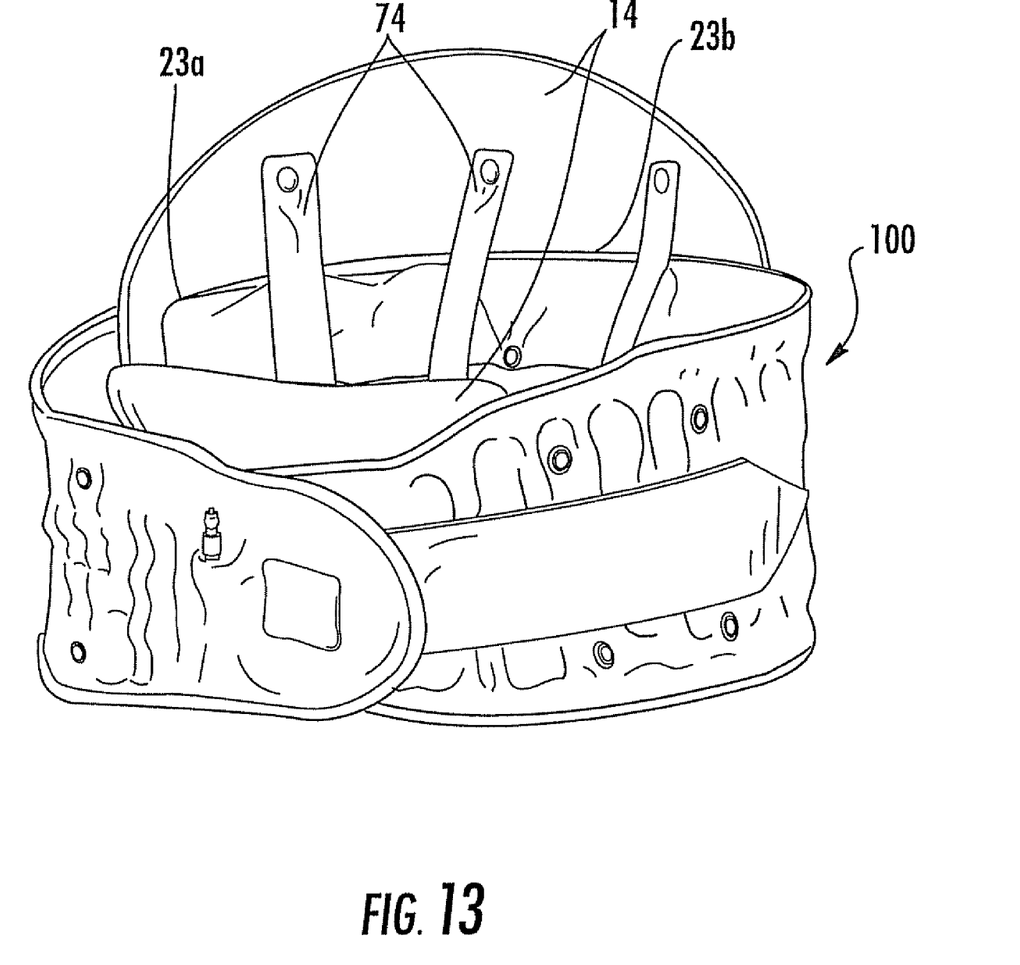
FIG. 13 is a top perspective view of another embodiment of a spinal brace.
Figure 14:
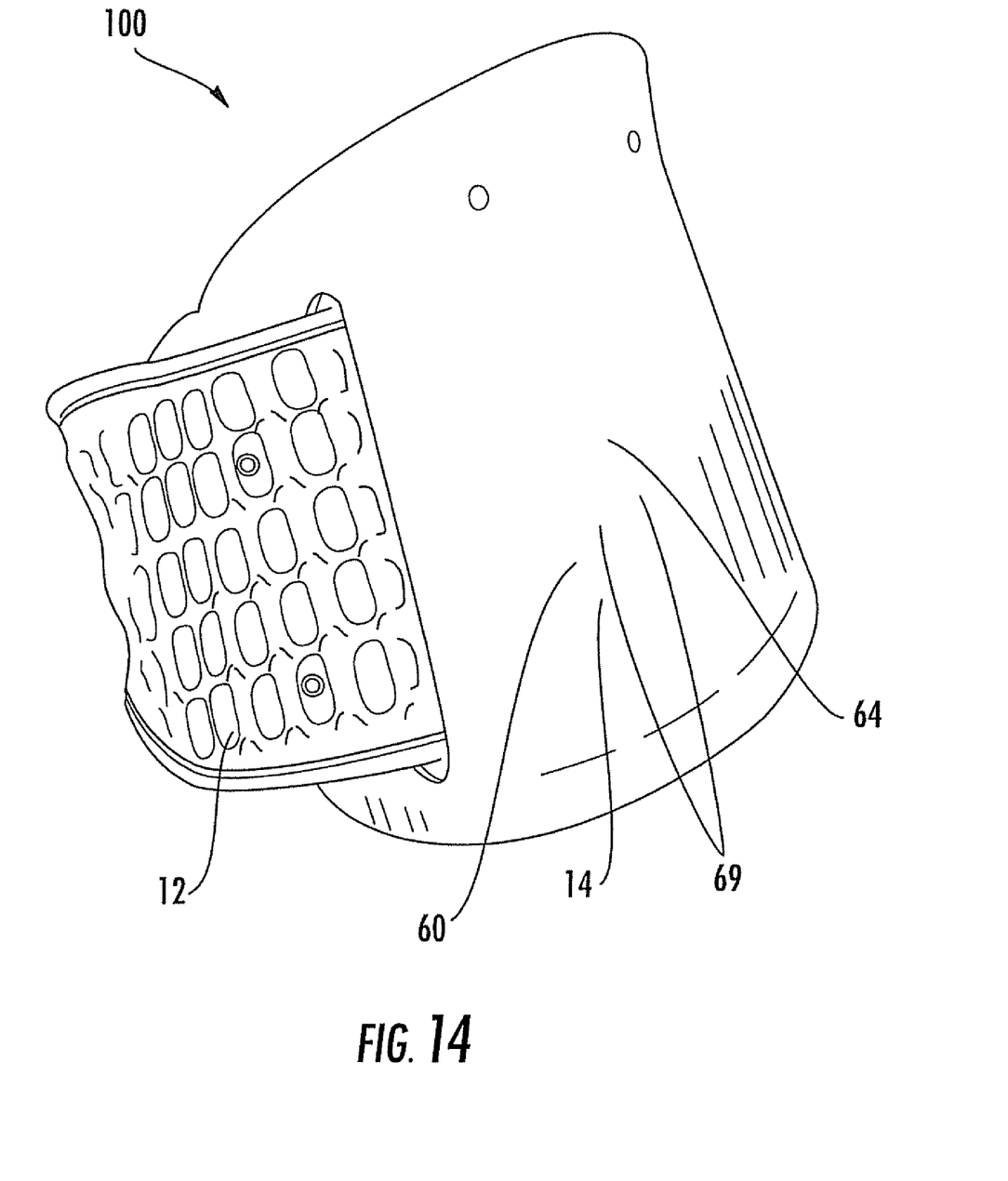
FIG. 14 is another top perspective view of the spinal brace of FIG. 13.

Referring to FIGS. 13 and 14, another exemplary embodiment 100 of the spinal brace 10 is illustrated, wherein like elements will be numbered as they are numbered above. In this embodiment 100, the geometry 56 of the posterior panel 52 includes a convexity 60 bulging towards a slope of the user's lumbar region, with the convexity having an apex 64 at a relative vertical midpoint 66 of the panel 52. The posterior panel 52 also defines flexibility openings 69 that are configured to facilitate lateral movement of the user 18. Also in this embodiment, in addition to the associating openings 23-b, the band 12 may also be associated with the panel 52 via at least one strap 74 disposed on the inner surface 68a of the panel 52.

Figure 15:
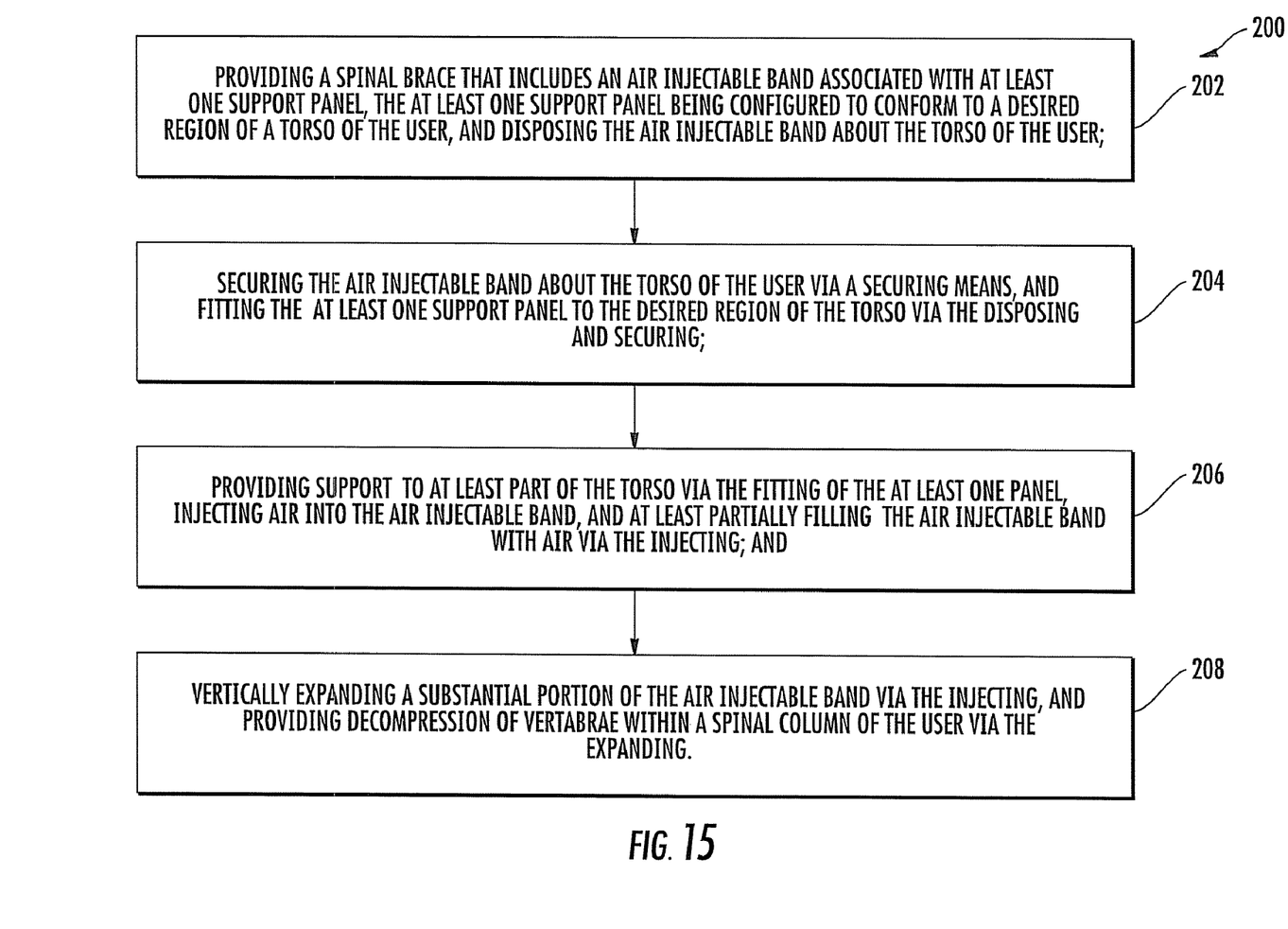
FIG. 15 is a block diagram illustrating a method for bracing a spine of a user.

Referring to FIG. 15, a block diagram illustrating a method 200 for bracing a spine of a user is illustrated and includes providing a spinal brace 10 that includes an air injectable band 12 associated with at least one support panel 14, the at least one support panel 14 being configured to conform to a desired region of a torso 16 of the user 18, and disposing the air injectable band 12 about the torso 16 of the user 18, as shown in operational block 202. The method 200 also includes securing the air injectable band 12 about the torso 16 of the user 18 via a securing means 48, and fitting the at least one support panel 14 to the desired region of the torso 16 via the disposing and securing, as shown in operational block 204. The method 200 further includes providing support to at least part of the torso 16 via the fitting of the at least one panel 14, injecting air into the air injectable band 12, and at least partially filling the air injectable band 12 with air via the injecting, as shown in operational block 206. The method 200 additionally includes vertically expanding a substantial portion 25 of the air injectable band 12 via the injecting, and providing decompression of vertebrae within a spinal column of the user 18 via the expanding, as shown in operational block 208.

While the invention has been described with reference to an exemplary embodiment, it should be understood by those skilled in the art that various changes may be made and equivalents may be substituted for elements thereof without departing from the scope of the invention. In addition, many modifications may be made to adapt a particular situation or substance to the teachings of the invention without departing from the scope thereof. Therefore, it is important that the invention not be limited to the particular embodiment disclosed as the best mode contemplated for carrying out this invention, but that the invention will include all embodiments falling within the scope of the apportioned claims. Moreover, unless specifically stated any use of the terms first, second, etc. do not denote any order or importance, but rather the terms first, second, etc. are used to distinguish one element from another.

What is claimed is:

1. A spinal brace comprising:
a flexible air injectable band configured to be disposed about a torso of a user and to provide traction to a spine of the user;
a support panel configured to provide support by compression to at least a region of said torso, said support panel being less flexible than said air injectable band; and
means of associating said support panel with said flexible air injectable band;
wherein the air injectable band is configured to expand in an axis generally parallel to the spine when inflated so as to apply a force at a rib area of the user via an upper edge and a force at a hip area via a lower edge to provide said traction comprising a decompression of vertebrae within the spinal column of the user; and
wherein said means of associating comprise two association openings formed through the support panel, one association opening disposed at each of substantially opposite ends of said support panel, the air injectable band extending through the association openings, wherein the association openings traverse across the support panel in a direction generally parallel to the spine and wherein said association openings have a dimension in said direction that is greater than a corresponding dimension of the flexible air injectable band.

2. The brace of claim 1, wherein said support panel comprises a posterior panel, the brace further comprising an anterior panel.

3. The brace of claim 2, wherein said means of associating further comprises a hook and loop attachment material disposed on an inner surface of said anterior panel and an outer surface of said air injectable band.

4. The brace of claim 2, wherein said means for associating further includes a strap disposed on an inner surface of said posterior panel.

5. The brace of claim 2, wherein said posterior panel defines a flexibility opening in the panel, said flexibility opening being configured to facilitate lateral movement of said user.

6. The brace of claim 1, wherein the air injectable band includes an air injectable tube and a securing cover, said air injectable tube being disposed within and attached to said securing cover.

7. The brace of claim 6, wherein said air injectable band includes an expandable portion, and said air injectable tube is positioned in said securing cover to extend in a grid pattern substantially across an entire length of the expandable portion.

8. The brace of claim 7, wherein said grid pattern is configured to vertically expand said air injectable tube and said expandable portion when air is injected into said air injectable tube.

9. The brace according to claim 8, wherein said air injectable tube is an elastic material, said air injectable tube being configured to return to a relaxed state when said air is released from said air injectable tube.

10. The brace of claim 6, wherein an air inlet and exit valve is installed at an end of said air injectable tube and extends from said cover of said band, said valve being associable with a pump.

11. The brace of claim 6, wherein at least an inner surface of said securing cover comprises a non-abrasive material.

12. The brace of claim 1, wherein said injectable band includes a securing strap extending from an end of said band, said end of said band and said securing strap including a securing means for securing the brace around said torso.

13. The brace of claim 12, wherein said securing means comprises at least one of a hook and loop attachment arrangement, at least one snap, belt, and button.

14. The brace of claim 1, wherein said support panel is composed of a rigid or semi-rigid material.

15. The brace of claim 1, wherein said support panel includes a geometry configured to conform to a desired region of said torso of said user.

16. The brace of claim 1, wherein said region of said torso is a lumbar region of said user.

17. The brace of claim 1, wherein said flexible air injectable band is configured to increase intervals between intervertebral discs said user and providing a decompression of vertebrae within a vertebral column of said user.

18. A spinal brace comprising:
an air inflatable portion configured to be disposed generally around a torso of a user, the air inflatable portion including an upper edge and an opposing lower edge configured such that, when the brace is worn by the user, the upper edge generally contacts a rib area of the user and the lower edge generally contacts a hip area of the user;
a support portion having a greater rigidity than the air inflatable portion and being configured such that, when the brace is worn by the user, the support portion is generally disposed at least at a back area of the user; and
an associating element configured to associate the air inflatable portion with the support portion;
wherein the inflatable portion is further configured to expand generally in a vertical axis when inflated so as to apply a force at the rib area via the upper edge and a force at the hip area via the lower edge to provide a decompression of vertebrae within a spinal column of the user;
wherein the support portion, in combination with the air inflatable portion, is further configured to compress the torso when the brace is worn; and
wherein said associating element comprises two association openings formed through the support portion, one association opening disposed at each of substantially opposite ends of said support portion, the air inflatable portion extending through the association openings, wherein the association openings traverse across the support portion in a direction generally parallel to the spine and wherein said association openings have a dimension in said direction that is greater than a corresponding dimension of the flexible air inflatable portion.

19. A method for bracing a spine of a user, the method comprising:
providing a spinal brace that includes an air injectable band associated with a support panel, said air injectable band extending through two association openings formed through said support panel, said openings formed at opposite ends of said support panel and traversing across the support panel in a direction generally parallel to the spine, the openings having a dimension in said direction greater than a corresponding dimension of the air injectable band, said support panel being configured to conform to a desired region of a torso of the user;
disposing said air injectable band about said torso of the user;
securing said air injectable band about said torso of the user via a securing means;
fitting said support panel to said desired region of said torso via said disposing and securing;
providing support by compression to at least part of said torso via said fitting of said panel;
injecting air into said air injectable band, and at least partially filling said air injectable band with air via said injecting;
vertically expanding a substantial portion of said air injectable band within said association openings via said injecting; and
providing decompression of vertebrae within a spinal column of the user via said expanding.

* * * * *